US007052511B2

(12) United States Patent
Weldon et al.

(10) Patent No.: US 7,052,511 B2
(45) Date of Patent: May 30, 2006

(54) DELIVERY SYSTEM AND METHOD FOR DEPLOYMENT OF FORESHORTENING ENDOLUMINAL DEVICES

(75) Inventors: James Weldon, Roslindale, MA (US); Ilya Yampolsky, West Roxbury, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 547 days.

(21) Appl. No.: 10/115,669

(22) Filed: Apr. 4, 2002

(65) Prior Publication Data

US 2003/0191516 A1    Oct. 9, 2003

(51) Int. Cl.
*A61F 2/06* (2006.01)

(52) U.S. Cl. .................. 623/1.11; 606/194; 606/200

(58) Field of Classification Search ............... 623/1.11, 623/1.12; 606/191–200
See application file for complete search history.

(56) References Cited

U.S. PATENT DOCUMENTS

| | | | | |
|---|---|---|---|---|
| 2,722,931 A | * | 11/1955 | May ........................ | 604/68 |
| 4,474,572 A | * | 10/1984 | McNaughton et al. ...... | 606/117 |
| 4,655,771 A | | 4/1987 | Wallsten | |
| 5,383,892 A | * | 1/1995 | Cardon et al. .............. | 606/198 |
| 5,415,664 A | | 5/1995 | Pinchuk | |
| 5,433,723 A | | 7/1995 | Lindenberg et al. | |
| 5,707,376 A | * | 1/1998 | Kavteladze et al. ........ | 623/1.11 |
| 5,968,052 A | | 10/1999 | Sullivan, III et al. | |
| 6,143,021 A | | 11/2000 | Staehle | |
| 6,371,963 B1 | * | 4/2002 | Nishtala et al. ............. | 606/113 |
| 6,527,779 B1 | * | 3/2003 | Rourke ........................ | 606/108 |

FOREIGN PATENT DOCUMENTS

| | | |
|---|---|---|
| EP | 0 747 021 A2 | 12/1996 |
| EP | 1 078 611 A1 | 2/2001 |
| WO | WO 00/18330 | 4/2000 |
| WO | WO 02/03888 A2 | 1/2002 |

OTHER PUBLICATIONS

International Search Report for corresponding PCT/US03/08436 application, date of mailing Aug. 5, 2003.
U.S. Appl. No. 09/442,165, filed Nov. 16, 2002, by Paul F. Chouinard et al.
U.S. Appl. No. 09/574,418, filed May 19, 2000, by Jason R. Sullivan et al.

* cited by examiner

*Primary Examiner*—Julian W. Woo
*Assistant Examiner*—Sarah Webb
(74) *Attorney, Agent, or Firm*—RatnerPrestia (57) ABSTRACT

A delivery system comprising an endoluminal device, an outer sheath that radially surrounds the endoluminal device, a pusher positioned at one end of the endoluminal device, and a linkage between the pusher and the outer sheath that coordinates movement of the outer sheath in a first direction with simultaneous movement of the pusher in a second direction opposite the first direction. This delivery system is particularly useful for endoluminal devices that foreshorten, and may comprise the outer sheath moving a first distance ($d_1$) and the pusher moving a second distance ($d_2$), where $d_2/d_1$ is approximately equal to the foreshortening ratio. The delivery system of this invention enables a foreshortening device, such as a vena cava filter, or stent, graft, or combination thereof, to be deployed with its end in a precise deployment location without foreshortening causing the end to move from the deployment location as the stent expands.

38 Claims, 5 Drawing Sheets

DELIVERY SYSTEM AND METHOD FOR DEPLOYMENT OF FORESHORTENING ENDOLUMINAL DEVICES

TECHNICAL FIELD

This invention relates generally to delivery systems for endoluminal devices, and, more specifically, to delivery systems for endoluminal devices that undergo a decrease in length when being expanded from a radially compressed configuration.

BACKGROUND OF THE INVENTION

Endoluminal devices comprise the general category of devices, such as stents, grafts, combinations thereof commonly referred to as stent-grafts or endoluminal prostheses, vena cava filters, and the like, that may be implanted in a body lumen. Endoluminal devices may be implanted by so-called "minimally invasive techniques" in which the prosthesis, restrained in a radially compressed configuration by a sheath or catheter, is delivered by a deployment system or "introducer" to the site where it is required. The introducer may enter the body through the patient's skin, or by a "cut down" technique in which the entry lumen, such as a blood vessel, is exposed by minor surgical means. When the introducer has been threaded into the body lumen to the prosthesis deployment location, the introducer is manipulated to cause the endoluminal device to be ejected from the surrounding sheath or catheter in which it is restrained (or alternatively the surrounding sheath or catheter is retracted from the endoluminal device), whereupon the endoluminal device expands to a predetermined diameter at the deployment location, and the introducer is withdrawn.

As referred to herein, "distal" refers to the direction further away from the insertion point and "proximal" refers to the direction closer to the insertion point. Endoluminal devices, such as stents and vena cava filters, may expand by spring elasticity, balloon expansion, or by the self-expansion of a thermally or stress-induced return of a memory material to a pre-conditioned expanded configuration.

Various types of endoluminal device architectures, are known in the art, including many designs comprising a filament or number of filaments, such as a wire or wires, wound or braided into a particular configuration. Included among these configurations are braided stents, such as is described in U.S. Pat. No. 4,655,771 to Hans I. Wallsten and incorporated herein by reference; the '771 Wallsten patent is only one example of many variations of braided architecture known in the art and thus is not intended as a limitation of the invention described herein later. Braided endoluminal devices tend to be very flexible, having the ability to be placed in tortuous anatomy and still maintain patency. The flexibility of braided stents make them particularly well-suited for treating aneurysms in the aorta, where often the lumen of the vessel becomes contorted and irregular both before and after placement of the stent.

Figure 1A:
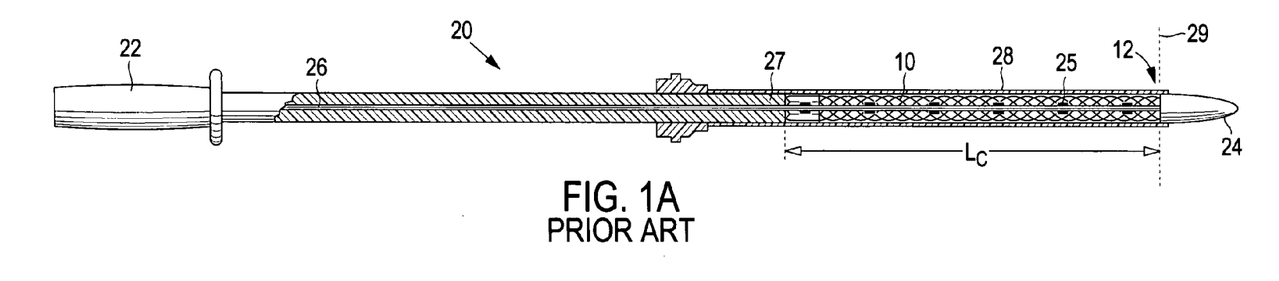
FIG. 1A depicts a partial longitudinal section of an exemplary delivery system of the prior art for deploying a foreshortening-prone stent of the prior art.
Figure 1B:
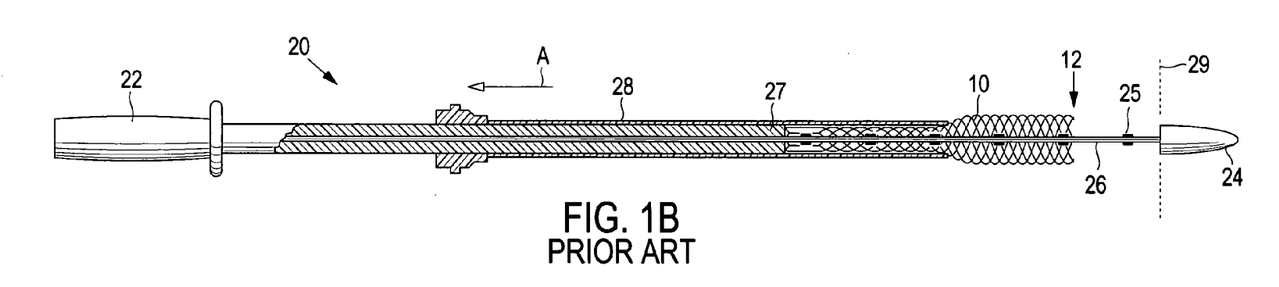
FIG. 1B depicts the delivery system of FIG. 1A in a partially deployed configuration.
Figure 1C:
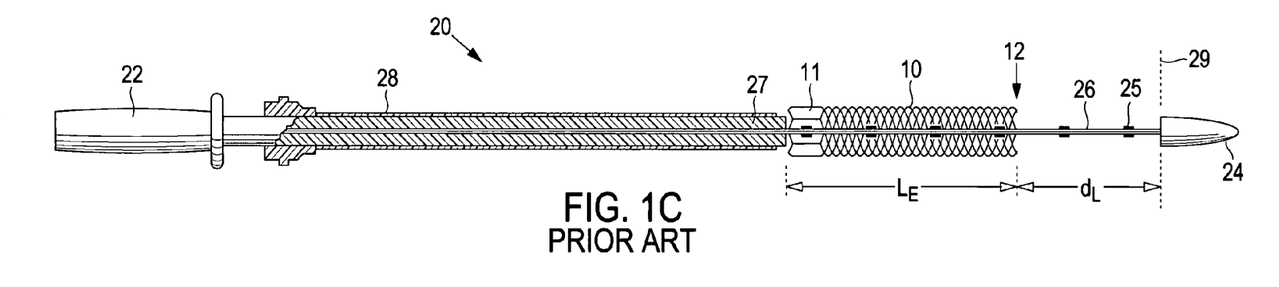
FIG. 1C depicts the delivery system of FIG. 1A after the stent has been fully deployed.

Many braided endoluminal devices experience "foreshortening" when deployed in a body lumen. Referring now to FIGS. 1A–1C, showing an exemplary delivery system 20 of the prior art, stent 10 may have a first length $L_C$ when radially compressed as shown in FIG. 1A and a second, shorter length $L_E$ when radially expanded, as shown in FIG. 1C. The "foreshortening ratio"

$$\frac{L_C - L_E}{L_E}$$

can be used as a measure of the relative change in length. Braided endoluminal devices typically have a relatively large foreshortening ratio as compared to non-braided endoluminal devices. The foreshortening ratio is a function of compressed diameter, deployed diameter, and the braid angle. If these variables are known, the endoluminal device has a predictable foreshortening ratio.

Foreshortening may affect the deployment accuracy of endoluminal devices. Describing delivery system 20 now in more detail, the delivery system comprises a handle 22, a tip 24, an inner member 26 attached to the tip and the handle, a pusher 27 positioned proximally of stent 10, and an outer sheath 28 slidable relative to the inner member and pusher. Inner member 26 may have one or more protrusions 25 thereon for engaging the stent during deployment, such as are disclosed in U.S. Pat. No. 6,607,551 to Sullivan et al., incorporated herein by reference. Stent 10 may be a braided stent having a wound end 11, such as is described in U.S. Pat. No. 6,585,758 to Chouinard et al. and incorporated herein by reference. Delivery system 20 is maneuvered into the body lumen (not shown) so that the distal end 12 of stent 10 is aligned with a desired deployment location 29 in the lumen, as shown in FIG. 1A. FIGS. 1A–1C are shown in vertical alignment with one another on the page so that desired deployment location 29 is in the same horizontal position in all figures for illustrative purposes.

To deploy the stent, outer sheath 28 is retracted in the direction of arrow A as shown in FIG. 1B. As stent 10 begins to deploy, it also foreshortens, causing distal end 12 of stent 10 to be move proximally from the desired deployment location 29. Thus, after full deployment as shown in FIG. 1C, continued foreshortening during deployment may cause the ultimate resting position of distal end 12 to be a distance $d_L$ from the desired deployment location 29. This distance $d_L$ is typically approximately the difference in length between the radially compressed length $L_C$ and the expanded length $L_E$. In some cases, distal end 12 of stent 10 may frictionally engage a portion of the body lumen in which the stent is being deployed before the stent is completely deployed. In such cases, a portion of the length accounting for the difference between the compressed length $L_C$ and the expanded length $L_E$ of the stent will be proximal to the deployed stent. Thus, even though this distance may be predictable, practitioners must determine the correct place to start deployment based upon where the end of the stent is expected to land after foreshortening. Deploying such stents with accuracy, therefore, takes repeated practice and is prone to error.

It is therefore desirable to minimize the impact of foreshortening of braided endoluminal devices during deployment so that such endoluminal devices can be more accurately deployed.

SUMMARY OF THE INVENTION

One aspect of the invention comprises a delivery system for an endoluminal device, such as a vena cava filter, or stent, graft, or combination thereof. The delivery system comprises an endoluminal device having a compressed configuration, an outer sheath that radially surrounds the endoluminal device in its compressed configuration, a pusher positioned at one end of the endoluminal device, and a linkage between the pusher and the outer sheath that coordinates movement of the outer sheath in a first direction with simultaneous movement of the pusher in a second direction opposite the first direction. This delivery system is particularly useful for endoluminal devices having a compressed length ($L_C$), an expanded length ($L_E$), and a foreshortening ratio $$\left(\frac{L_C - L_E}{L_E}\right)$$

greater than 0. In such an embodiment, the linkage preferably coordinates a first distance of proximal retraction ($d_1$) of the outer sheath with a second distance ($d_2$) of distal advancement of the pusher, so that the second distance divided by the first distance $$\left(\frac{d_2}{d_1}\right)$$

is approximately equal to the foreshortening ratio. The linkage may provide mechanical advantage that enables a user to manipulate the linkage using less force than is required to simultaneously move the outer sheath in the first direction and the pusher in the second direction.

In one aspect of the invention, the linkage may comprise a rack and pinion system. The rack and pinion system comprises a first rack in communication with the outer sheath, a second rack in linear communication with the pusher, and a pair of rotationally-interlocked pinions supported between the first rack and the second rack. The pair of rotationally-interlocked pinions comprise a first pinion having a first diameter adapted to interface with the first rack and a second pinion having a second, relatively smaller diameter adapted to interface with the second rack. A member, such as a dial with a larger diameter than the first pinion, may be rotationally interlocked to the pinions for rotating the pinions to cause the outer sheath and the pusher to simultaneously move. The system may comprise a casing disposed about the linkage, and a bearing in the casing for supporting a shaft on which the pinions are mounted.

In another aspect of the invention, the linkage comprises a screw shaft having a first threaded flight having a first pitch and a second threaded flight having a second pitch. A first traveler is engaged by the first threaded flight and in linear communication with the outer sheath. A second traveler is engaged by the second threaded flight and in linear communication with the pusher. The linkage further comprises means for turning the screw shaft. Where the first threaded flight has a first pitch ($P_1$) corresponding to a number of turns per unit length and a second threaded flight having a second corresponding pitch ($P_2$), the ratio of the first pitch to the second pitch ($P_1/P_2$) is approximately equal to the foreshortening ratio.

In some embodiments of the invention, the delivery system may further comprise a clutch mechanism for preventing simultaneous movement of the outer sheath and the pusher when engaged, including, optionally, indicia for indicating to a user of the delivery system when to engage or disengage the clutch mechanism. Other embodiments may comprise a lag mechanism for preventing simultaneous movement of the outer sheath and the pusher over a predetermined travel distance of the outer sheath.

Another aspect of the invention comprises a manipulator for a delivery system comprising an outer sheath that radially surrounds a compressed endoluminal device and a pusher positioned at one end of the endoluminal device. The manipulator comprises a first interface for connecting the manipulator in communication with the outer sheath, a second interface for connecting the manipulator in communication with the pusher, a linkage coupled to the first and second interface for coordinating movement of the outer sheath in a first direction with simultaneous movement of the pusher in a second direction opposite the first direction, and means for actuating the linkage. The manipulator may be detachable from the delivery system and reusable, in which case the manipulator comprises a material of construction, such as but not limited to stainless steel, adapted to withstand prolonged exposure to high temperatures effective to sterilize the manipulator without being damaged.

Still another aspect of the invention comprises a method for endoluminal deployment of an endoluminal device. The method comprises first introducing a delivery system from a first location outside a lumen to a second location inside the lumen. The delivery system comprises an endoluminal device in a compressed configuration, an outer sheath that radially surrounds the endoluminal device in the compressed configuration, a pusher positioned at a first end of the endoluminal device, and a linkage in communication with the pusher and the outer sheath for coordinating simultaneous movement of the outer sheath and the pusher. The second location is a location at which a second end of the endoluminal device is axially aligned with a desired target location on the lumen. The method next comprises deploying the endoluminal device so that the second end is implanted in the desired target location. This is effected by manipulating the linkage to move the outer sheath in a first direction while simultaneously moving the pusher in a second direction opposite the first direction.

Where the first location outside the lumen is a proximal location, the second location is a distal location, the first direction is a proximal direction and the second direction is a distal direction, the step of deploying the endoluminal device may comprise proximally retracting a handle in communication with the outer sheath or distally advancing a slide in communication with the pusher. Where the linkage comprises a rack and pinion system, the step of deploying the endoluminal device may comprise manipulating a member that is rotationally interlocked with the pinion. Where the stent delivery system comprises a first component comprising the outer sheath and the pusher and a second, detachable component comprising the linkage, the method may comprise attaching the first component to the second component before introducing the delivery system into the lumen. Similarly, the method may comprise the steps of detaching the second component from the first component after deployment of the endoluminal device and then sterilizing the second component so that it can be reused.

In an embodiment wherein the endoluminal device has a foreshortening ratio greater than zero in the first portion and the foreshortening ratio equal to zero in a second portion and the system further comprises a clutch mechanism for preventing simultaneous movement of the outer sheath and the pusher when engaged, the method comprises deploying the first portion of the endoluminal device with the clutch engaged so that there is not simultaneous movement of the outer sheath and the pusher, and deploying the second portion of the endoluminal device with the clutch released so that there is simultaneous movement of the outer sheath and the pusher. In an embodiment wherein the endoluminal device has a foreshortening ratio greater than zero in a first portion and a foreshortening ratio equal to zero in a second portion and the system comprises a lag mechanism for preventing simultaneous movement of the outer sheath and the pusher over a predetermined travel distance of the outer sheath, the method comprises deploying the first portion of the endoluminal device without simultaneous movement of the outer sheath and the pusher and deploying the second portion of the endoluminal device with simultaneous movement of the outer sheath and the pusher.

It is to be understood that both the foregoing general description and the following detailed description are exemplary, but are not restrictive, of the invention.

BRIEF DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

Figure 2A:
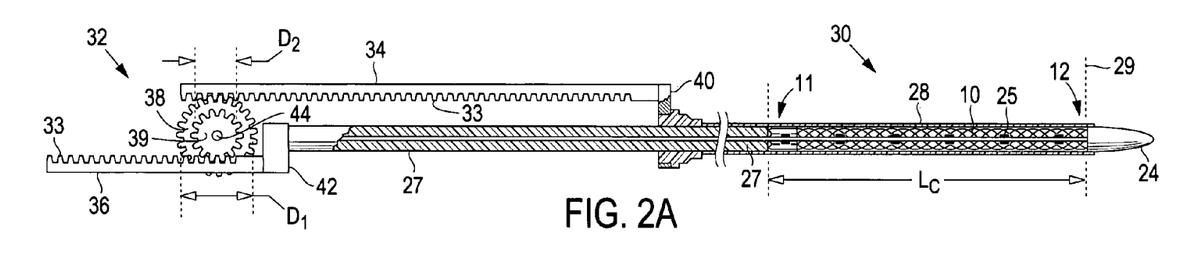
FIG. 2A depicts a partial longitudinal section of an exemplary delivery system of the present invention.
Figure 2B:
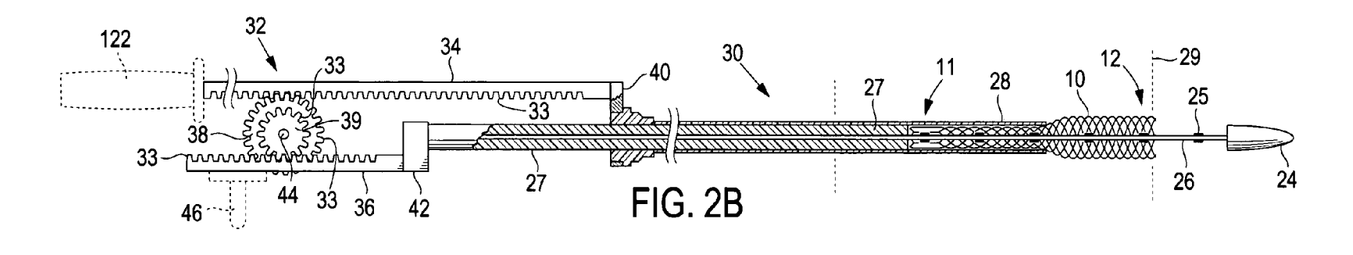
FIG. 2B depicts the delivery system of FIG. 2A in a partially deployed configuration.
Figure 2C:
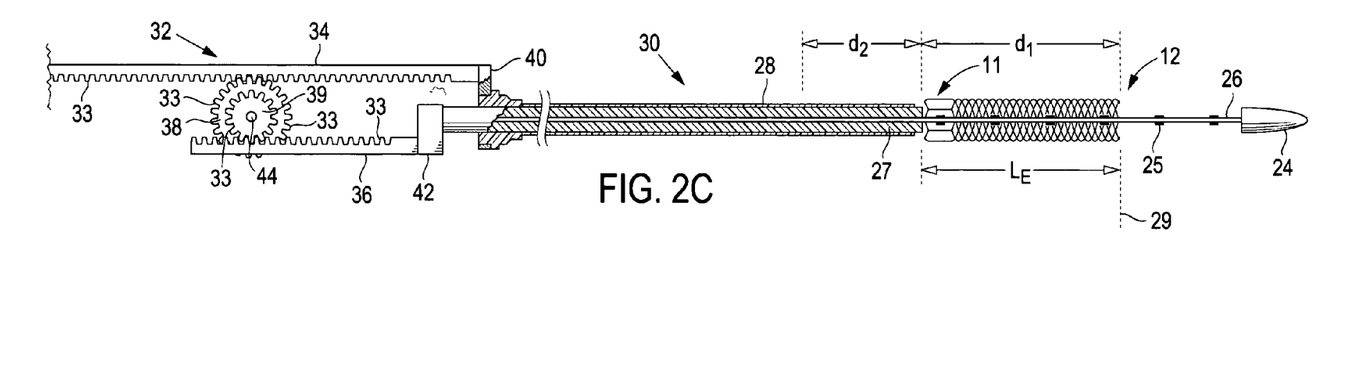
FIG. 2C depicts the delivery system of FIG. 2A after the stent has been fully deployed.

Referring now to FIGS. 2A–2C, there is shown an exemplary delivery system 30 of this invention in various stages of deployment. Delivery system 30 comprises stent 10 in its compressed configuration, outer sheath 28 that radially surrounds the stent, pusher 27 positioned at the proximal end 11 of the stent, and a linkage 32 in communication with both the pusher and the outer sheath. Linkage 32 coordinates proximal retraction of outer sheath 28 with simultaneous distal advancement of pusher 27. Also shown in FIGS. 2A–2C is inner member 26, attached to an interface 42 at its proximal end and extending axially through stent 10 and pusher 27 to a connection with tip 24 at its distal end.

As shown in FIGS. 2A–2C, linkage 32 comprises a rack and pinion system having intermeshing teeth 33. The rack and pinion system comprises a first rack 34 in linear communication with outer sheath 28, a second rack 36 in linear communication with the pusher 27, and a pair of rotationally-interlocked pinions 38 and 39 supported between the first rack and the second rack. Pinion 38 has a first diameter $D_1$ and is adapted to interface with the rack 34. Pinion 39 has a second diameter $D_2$ that is relatively smaller than first diameter $D_1$, and is adapted to interface with the rack 36. It should be noted that the rack and pinion system shown in FIGS. 2A–2C is merely one exemplary embodiment, and other rack and pinion systems may also be devised to provide a similar effect. For example, the pinions may have a common diameter and may be mounted on separate shafts, with a gear mechanism, belt and sheave, or chain and sprocket mechanism provided between the pinions to provide the differential motion between the racks.

The term "linkage" is used herein to denote any mechanism that links together the motion of outer sheath 28 and pusher 27. Thus, although a rack and pinion system is shown herein, other types of linkages may be provided within the scope of this invention, including but not limited to those discussed specifically herein below.

By "in linear communication with" it is meant that the each rack 34 and 36 moves linearly in concert with the sheath 28 or the pusher 27, respectively, such that movement of the respective rack in one linear direction will move the sheath or pusher in the same linear direction. Although rack 34 is shown with a direct connection to sheath 28 at interface 40 and rack 36 is shown with a direct connection to pusher 27 at interface 42 in FIGS. 2A–2C, the respective racks may be indirectly connected to the sheath or pusher through one or more intermediate elements. Thus, the terminology "in linear communication with" has been chosen to reflect that no direct connection between the racks and the sheath or pusher is required. Preferably, interfaces 40 and 42 are configured to be attached to sheath 28 and pusher 27 at a location such that the interfaces and linkage 32 can remain outside of the body lumen during deployment.

By "rotationally interlocked" it is meant that pinions 38 and 39 are connected in such a way that they rotate the same degree of revolution in the same direction simultaneously. For example, as shown in FIGS. 2A–2C, the pinions are mounted on the same shaft 44 in a way that one full revolution of the shaft will coincide with one full revolution of both pinions 38 and 39. The pinions may be bonded together or may be machined from a single integral piece, or the shaft may be keyed and each pinion may be independent from one other but keyed similarly to the shaft. In an alternative embodiment, the pinions may be mounted on separate shafts, with other methods of rotationally interlocking them, such as a gear train or drive belt or chain that provides for one full revolution of one pinion to translate to one full revolution of the other pinion. It should be understood that any number of mechanisms may be devised for providing rotationally interlocking pinions, all of which are within the scope of the present invention.

Figure 3A:
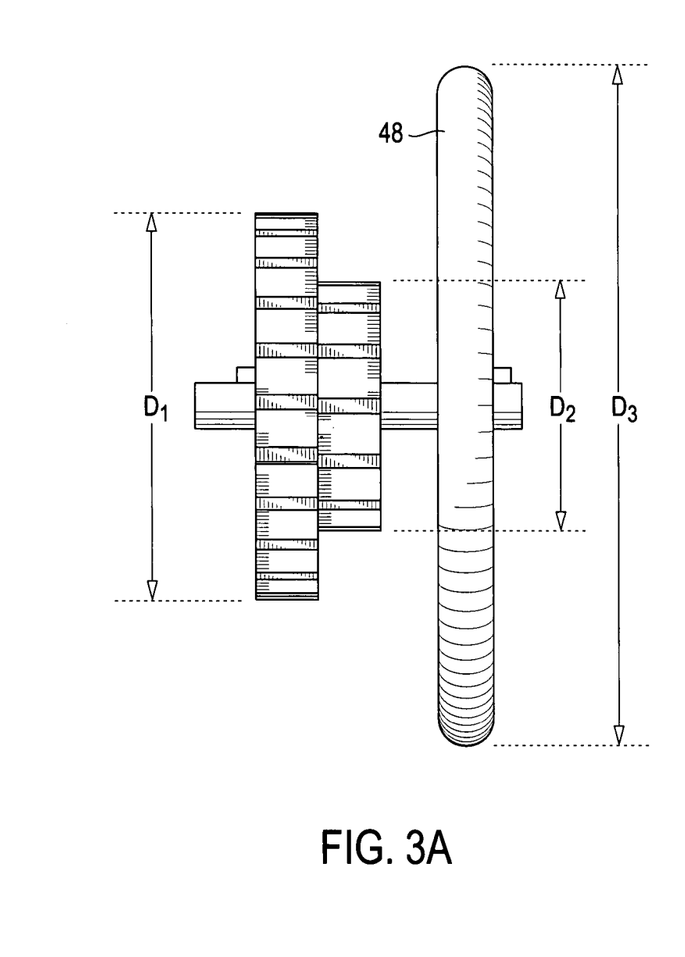
FIG. 3A is a proximal view of an exemplary embodiment wherein the pinions shown in FIG. 2A have a dial rotationally interlocked to them.
Figure 3B:
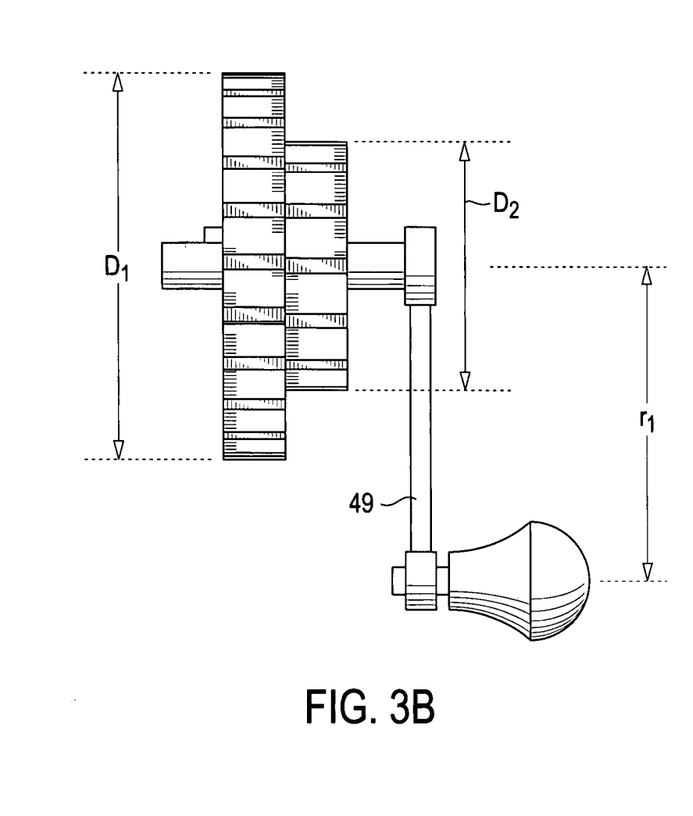
FIG. 3B is a proximal view of an exemplary embodiment wherein the pinions shown in FIG. 2A have a crank rotationally interlocked to them.

The simultaneous retraction of outer sheath 28 and advancement of pusher 27 may be accomplished by any of a number of methods and structures, some examples of which are shown in FIG. 2B with dashed lines, and in FIGS. 3A and 3B. As shown in FIG. 2B, a handle 122 may be attached to rack 34 or otherwise in linear communication with outer sheath 28 so that proximal retraction of the handle actuates the linkage. Similarly, a slide 46 may be attached to rack 36 or otherwise in linear communication with pusher 27, so that distal advancement of the slide will actuate the linkage. Although both handle 122 and slide 46 are both shown in FIG. 2B, embodiments of the invention may have none, both, or only one of these means. A member in rotational communication with pinions 38 and 39, such as dial 48 shown in FIG. 3A or crank 49 shown in FIG. 3B, may also or instead be used for directly rotating at least one of the pinions, thereby actuating the linkage. Suitable members are not limited to dial 48 and crank 49, but may include any means known in the art for actuating a pinion, such as for example but not limited to, a pistol grip mechanism such as disclosed in U.S. Pat. No. 5,968,052 to Sullivan and DeVries, incorporated herein by reference. By "in rotational communication" with pinions 38 and 39 it is meant that rotation of the member also causes pinions 38 and 39 to rotate. A full revolution of the first member may translate to less than, equal to, or greater than a full revolution of a second member in rotational communication with the first member.

Accordingly, a dial or crank may be rotationally interlocked to the pinions as shown in FIGS. 3A and 3B so that one revolution of the dial or crank corresponds to one rotation of the pinions, or the dial or crank may include a transmission such as a gearing mechanism that provides mechanical advantage, such as for example a dial geared to the pinion such that a full rotation of the dial results in less than a full rotation of the pinion. Conversely, if it is desired to reduce the amount of travel of the dial relative to the pinion, the transmission may translate less than a full rotation of the dial to a full rotation of the pinion. The diameter of the dial or diameter of rotation of the crank may also be used to provide mechanical advantage or to reduce travel. The "diameter of rotation" for a crank is twice the radial distance $r_1$ of the crank from the centerpoint of the shaft rotated by the crank, as shown in FIG. 3B. For example, dial 48 may have a diameter $D_3$ or crank 49 may have a diameter of rotation $2r_1$ greater than diameter $D_1$ of the largest pinion, as shown in FIGS. 3A and 3B, respectively. Where the dial is rotationally interlocked with the pinions, the larger diameter provides mechanical advantage. Conversely, a dial with a diameter smaller than diameter $D_1$ enables the user to retract outer sheath 28 a given linear distance greater than $\Phi \pi D_3$ by moving the dial a circumferential distance $\Phi \pi D_3$, where $\Phi$ is the percentage of a full revolution traveled by dial 48.

Figure 4:
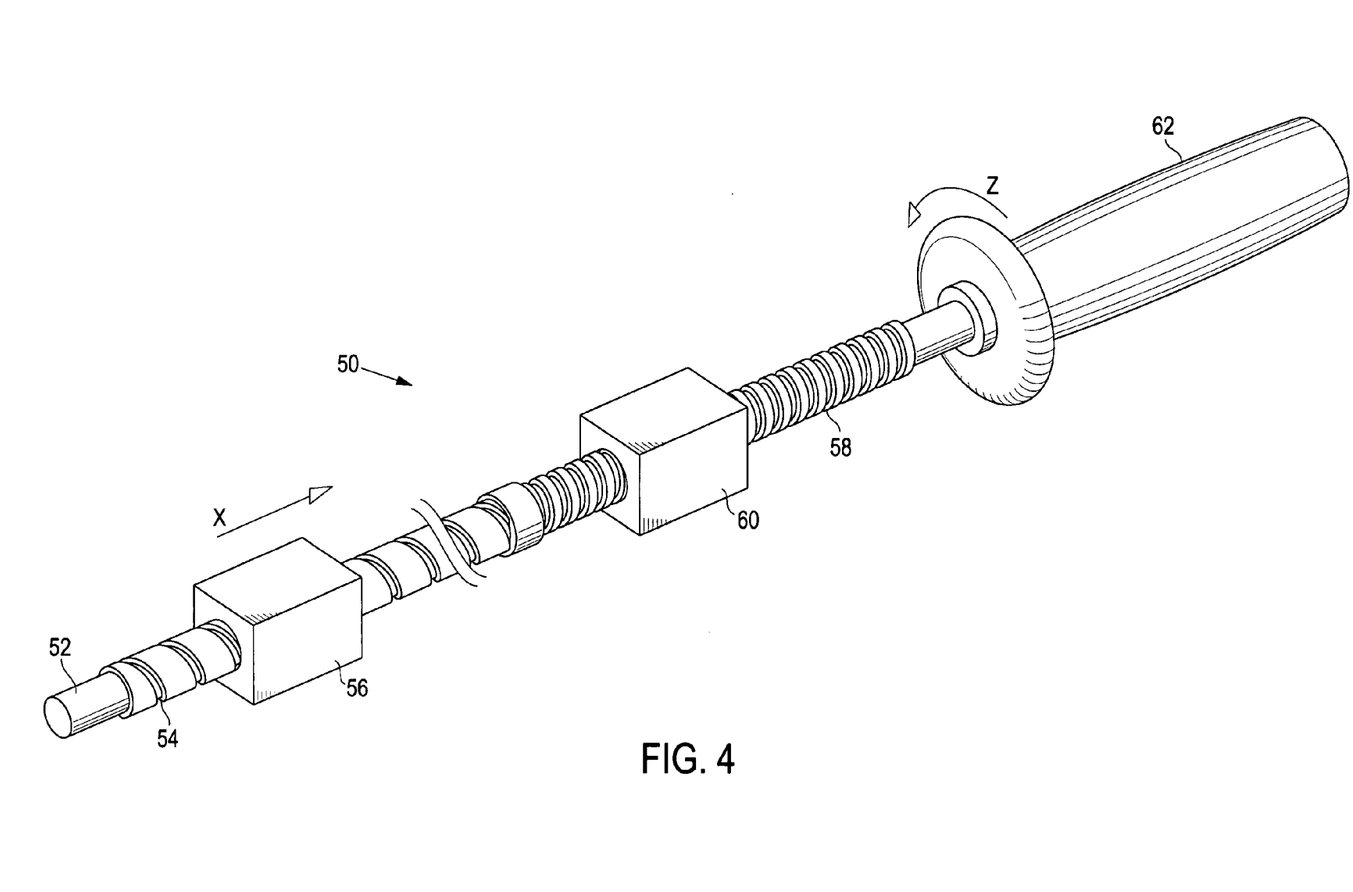
FIG. 4 is a perspective view of an exemplary linkage comprising a screw drive and a pair of travelers.

Referring now to FIG. 4, there is shown an alternative linkage embodiment 50 of the present invention comprising a screw shaft 52 having a first threaded flight 54 for engaging a first traveler 56, and a second threaded flight 58 for engaging a second traveler 60. A handle 62 may be used for manipulating the linkage. As shown in FIG. 4, when handle 62 is turned clockwise (as viewed from the handle end of the screw) in the direction of arrow Z, flight 54 moves traveler 56 in the direction of arrow X, whereas flight 58 moves traveler 60 in the direction opposite arrow X. Furthermore, flight 54 has a wider pitch than flight 58, so that traveler 56 moves a greater distance that traveler 60. Although illustrated herein with a single handle 62 that may be turned by the user, it should be recognized that any means for rotating screw shaft 52 may be provided. For example, screw shaft 52 may be engaged by a transmission for translating linear motion in any plane or rotational motion about any axis to rotational motion of screw shaft 52, with or without mechanical advantage, including engagement by, for example, the pistol grip mechanism referred to herein.

For any type of linkage used in the present invention, a preferred embodiment is for the linkage to coordinate a first distance ($d_1$) of proximal retraction of the outer sheath to a second distance ($d_2$) of distal advancement of the pusher. As shown in FIG. 2C, outer sheath 28 needs to retract a distance $d_1$ equal to the expanded length ($L_E$) of stent 10. By contrast, pusher 27 needs only to travel a distance $d_2$ equal to the compressed length ($L_C$) minus the expanded length ($L_E$). Therefore the ratio of the second distance to the first distance $$\left(\frac{d_2}{d_1}\right)$$

is equal to the foreshortening ratio.

For the rack and pinion system shown in FIGS. 2A–2C, the circumferential travel $\Phi \pi D_1$ of pinion 38 translates to distance $d_1$ and the circumferential travel $\Phi \pi D_2$ of pinion 39 translates to distance $d_2$ for an appropriate value of $\Phi$. Accordingly, the gear ratio $D_2/D_1$ is also preferably equal to the foreshortening ratio. Similarly, for the screw drive embodiment 50 shown in FIG. 4, where $P_1$ equals the pitch of flight 54 represented as a number of turns per unit length and $P_2$ equals the corresponding pitch of flight 58. Thus, the distance $d_1=n/P_1$, where n is the number of full turns of handle 62, and $d_2=n/P_2$. Accordingly, the ratio of $P_1/P_2$ is equal to the foreshortening ratio $d_2/d_1$.

The linkages of the present invention may comprise a separable component from the component comprising the outer sheath and pusher, or an inseparable component. As such, the linkage component may be described as a "manipulator" for a delivery system because it is used to manipulate the delivery system during deployment. The manipulator may comprise other components in addition to the linkage, but at a minimum, referring to the embodiment shown in FIGS. 2A–2C, the manipulator comprises linkage 32, interface 40 for connecting the manipulator in communication with the outer sheath 28, interface 42 for connecting the manipulator in communication with pusher 27, and means for actuating the linkage. The means for actuating the linkage may be any means known in the art, particularly those discussed above such as handle 122 or slide 46 as shown in FIG. 2B, or dial 48 or crank 49 as shown in FIGS. 3A and 3B, respectively. Finally, although a rack and pinion type linkage is shown herein by way of example, any type of linkage known in the art may be used, such as a belt and pulley system.

Where the manipulator is detachable from the rest of the delivery system, it may also be reusable. In such embodiments, it is desirable for the manipulator to comprise a material of construction adapted to withstand exposure to a predetermined temperature for a endoluminal device, however, a toothless portion of the rack may be most advantageous. The toothless portion 602 may be at the proximal end of the rack, a distal end of the rack, or in the middle of the rack, and the rack may have more than one toothless portion. The structural features of the lag system are preferably tailored to match the features of the endoluminal device to be deployed.

One advantage of a lag system over a clutch system, is that the rack can be designed so that the practitioner merely pulls proximally on rack 634, without having to be concerned about timing the engagement and release of the clutch. For clutch systems, however, the rack may be provided with indicia visible to the practitioner at the proximal end to indicate when to pull in the clutch and when to release. For example, in the clutch system, as rack 34 is retracted, a portion proximally protruding from the proximal end of the casing may comprise one color to indicate engaging the clutch and another color to indicate releasing the clutch. Thus, as the rack is retracted, the color of the rack emerging from the casing may indicate to the practitioner whether to engage or release the clutch. Similarly, dial 48 as shown in FIG. 3A may have color-coded portions or other indicia to indicate when to release and when to engage the clutch. In a crank system, the practitioner may be provided with instructions as to when to engage and disengage the clutch based on how many degrees the crank is turned. It should be recognized that for lag systems to work with respect to the dial or crank embodiments of FIG. 3A or 3B, respectively, the pinions are typically the members with toothless portions. A lag system for the screw shaft embodiment shown in FIG. 4 can be approximated by having a very close pitch for a predetermined portion of one of the flights.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. predetermined amount of time effective to sterilize the manipulator without the manipulator being damaged. For example, hospitals may heat items to be sterilized in an autoclave set to an effective temperature for an effective amount of time known to sterilize the items. The combination of time and temperature is well-known in the art, as are materials of construction suitable for items that undergo such sterilization procedures. Stainless steel is a typical material used, but the invention is not limited to any particular material, and therefore any suitable material known in the art may be used.

Manipulators not intended for reuse may comprise materials less expensive than stainless steel, as are known in the art, including materials such as plastics that can readily be incinerated in hospital incinerators. Although non-reusable manipulators may still be detachable if desired, for example for shipping or packaging considerations, manipulators that are integral to the rest of the stent delivery system may offer an advantageous reduction in assembly time and correspondingly reduced potential for assembly errors or failures at the interfaces.

The delivery system of the present invention lends provides a unique method for delivery of an endoluminal device. The method comprises the steps of first introducing the delivery system into a body lumen and aligning the first end of the endoluminal device to be deployed, which in FIG. 2A is the distal end 12, with a desired target location 29 on the lumen or a previously deployed endoluminal device (not shown). The method then comprises deploying the endoluminal device with the second end in the desired target location by manipulating the linkage to move the outer sheath in a first direction while simultaneously moving the pusher in a second direction opposite the first direction. Although as shown in FIGS. 2A–2C, the stent is being deployed from a proximal location outside the lumen into a distal location, and the outer sheath is proximally retracted while the pusher is distally advanced, the method is not limited to any particular direction of deployment. The step of manipulating the linkage may be initiated by retracting handle 122 or advancing slide 46 as shown in FIG. 2B, by turning dial 48 or crank 49 as shown in FIGS. 3A and 3B, respectively, or by any other means. Where the linkage provides mechanical advantage, the linkage may be manipulated using less force than the sum of forces required to move the outer sheath and the pusher without the linkage.

Although the method may be useful for the implantation of any endoluminal device, the method is particularly useful for an endoluminal device having a foreshortening ratio greater than 0. In such case, the method implants end 12 of the endoluminal device precisely at the desired target location 29, unlike methods of the prior art where the foreshortening of the endoluminal device causes the distal end to be implanted proximally of the desired target location. As discussed herein, the preferred method coordinating a first distance of proximal retraction ($d_1$) of outer sheath 28 with a second distance ($d_2$) of distal advancement of pusher 27 wherein the second distance divided by the first distance $$\left(\frac{d_2}{d_1}\right)$$

is approximately equal to the foreshortening ratio of the endoluminal device. It should be appreciated that although the illustrations and accompanying text herein refer to a stent, the introducer of the present invention may be used for deploying any type of endoluminal device, including but not limited to stents, grafts, prostheses, vena cava filters, and the like.

Where the component comprising the linkage is detachable from at least the outer sheath and the pusher, the method further comprises attaching the first component to the sheath and pusher component prior to introducing the stent delivery system into the lumen. Wherein the linkage component is reusable, the method further comprises the steps of detaching the second component from the first component after deployment of the stent and then sterilizing the linkage component.

Some stent or filter embodiments may comprise a combination of foreshortening and non-foreshortening sections. Thus, for example, deployment of one longitudinal section of the stent may benefit from the linkage between pusher and outer sheath as discussed above, whereas deployment of an adjacent longitudinal section may not benefit from such a linkage, and may actually suffer from use of such system. Thus, for this and other reasons, it may be desirable to provide a clutch mechanism that prevents engagement of the linkage when actuated. In other cases, the system may have structure features tailored to prevent advancement of the pusher simultaneously with retraction of the outer sheath at certain points during deployment. Exemplary such systems are described below, but the invention is not limited to any particular embodiment of these functionalities.

Figure 5:
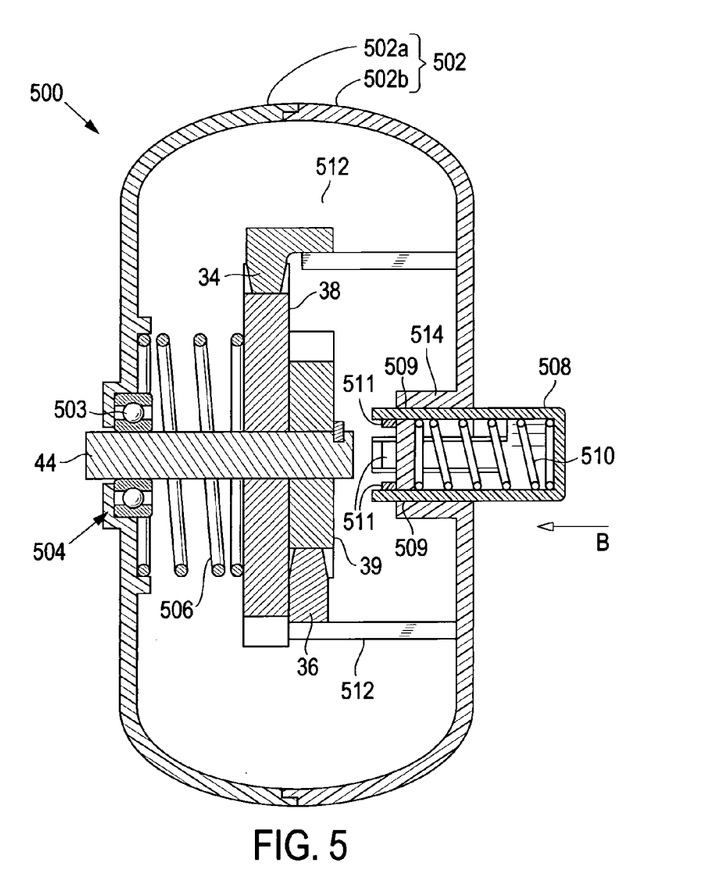
FIG. 5 is a cross-sectional view of a portion of an exemplary delivery system having a clutch mechanism.

Referring now to FIG. 5, there is shown a cross-sectional view of a portion of an exemplary delivery system 500 having a clutch mechanism. System 500 comprises a two part casing 502, comprising snap-together halves 502a and 502b. Ball bearing 504 having balls 503 is attached to half 502a, and shaft 44 is supported by the ball bearing. Although illustrated with a ball bearing, any type of bearing may be used. Spring 506 biases pinions 38 and 39 into a position in engagement with racks 34 and 36, respectively. Clutch button 508 is biased by spring 510 outwardly from casing half 502b, with stops 511 keeping the button from being fully ejected by the spring from the casing. Stops 511 may be set screws, a molded portion of the button, or any member functional to act as a stop but still provide for assembly of button 508 in the casing 502. Depressing button 508 inwardly in the direction of arrow B causes the inward-most portion of prongs 509 of button 508 to engage pinion 39 and push both pinions out of engagement with the racks for as long as the clutch button is depressed. Releasing button 508 allows spring 506 to force the pinions back into engagement with the racks. Casing half 502b has an indentation 514 concentric with button 508 so that button 508 can be depressed almost flush with casing 502. Button 508 may be circular, square, or any shape desired. Prongs 509 may comprise prongs with circular or square cross-sections, circumferential portions of a cylinder, or any shape known in the art.

Casing 502 is also shown with support brackets 512 for slidably supporting the racks. By "slidably supporting" it is meant that the brackets do not interfere with the distal and proximal sliding of the racks. It should be understood that even embodiments without a clutch mechanism may have a casing that supports the pinion shaft and that has brackets to support the travel of the racks. Such a casing may be a complete enclosure as shown in FIG. 5, or may provide only enough structure to support the racks and/or pinions. The invention is not limited to the particular features of the casing, nor to embodiments having casings. It should be understood, however, that typically some structural element is present to support the pinions in the desired position relative to the racks, and such supportive features have been omitted from FIGS. 2A–4 for simplicity of illustration. Such supportive features may comprise any structural elements known in the art.

Figure 6:
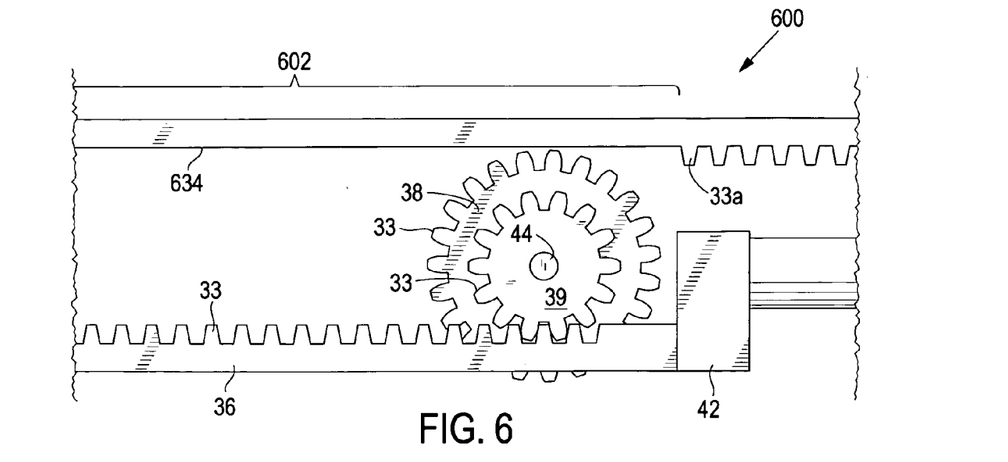
FIG. 6 depicts a partial longitudinal section of an exemplary delivery system of the present invention having a lag mechanism.

FIG. 6 illustrates an exemplary lag system 600. Lag system 600 comprises features similar to those found in FIGS. 2A–2C, except that a longitudinal portion 602 of rack 634 is without teeth 33. Thus, when rack 634 attached to outer sheath 28 is retracted over portion 602, there is nothing to engage pinion 38, and thus neither pinion 39 or 38 rotate until the proximal-most tooth 33a of rack 634 engages pinion 38. Thus, distal advancement of pusher 27 can be said to "lag" the proximal retraction of sheath 28. Toothless portion 602 may be tailored to have a length sufficient to deploy the corresponding non-foreshortening portion of the endoluminal device to be deployed. The toothless portion may also be on one of both of the pinions, if the conditions favor such an arrangement. Where the pinions experience more than a single revolution over the course of fully deploying the

What is claimed:

1. A delivery system for an endoluminal device, the delivery system comprising:
   an endoluminal device having a compressed configuration;
   an outer sheath that radially surrounds the endoluminal device in the compressed configuration;
   a pusher positioned at one end of the endoluminal device;
   a linkage, comprising a first pinion and a second pinion coaxially coupled to the first pinion, in communication with both the pusher and the outer sheath that coordinates movement of the outer sheath in a first direction with simultaneous movement of the pusher in a second direction opposite the first direction; and
   an actuatable clutch mechanism for preventing the simultaneous movement of the outer sheath and the pusher when engaged.

2. The delivery system of claim 1, wherein the endoluminal device has a compressed length ($L_C$), an expanded length ($L_E$), and a foreshortening ratio $$\left(\frac{L_C - L_E}{L_E}\right)$$

greater than 0.

3. The delivery system of claim 2, wherein the delivery system is adapted to deliver the endoluminal device from a proximal location outside a lumen to a distal location inside the lumen, the pusher is positioned at the proximal end of the stent, the first direction is a proximal direction, and the second direction is a distal direction.

4. The delivery system of claim 3, wherein the linkage coordinates a first distance of proximal retraction ($d_1$) of the outer sheath to a second distance ($d_2$) of distal advancement of the pusher.

5. The delivery system of claim 4, wherein the second distance divided by the first distance $$\left(\frac{d_2}{d_1}\right)$$

is approximately equal to the foreshortening ratio.

6. The delivery system of claim 1, wherein the linkage further comprises a rack to form a rack and pinion system.

7. The delivery system of claim 6, wherein the rack and pinion system comprises a first rack in linear communication with the outer sheath, a second rack in linear communication with the pusher, and the first pinion and the second pinion are rotationally-interlocked and supported between the first rack and the second rack, the first pinion having a first diameter adapted to interface with the first rack and the second pinion having a second, relatively smaller diameter adapted to interface with the second rack.

8. The delivery system of claim 7, further comprising a casing disposed about the linkage, and a bearing in the casing for supporting a shaft on which the pinions are mounted.

9. The delivery system of claim 8, wherein the casing further comprises one or more first inwardly disposed brackets for slidably supporting the first rack and one or more second inwardly disposed brackets for slidably supporting the second rack.

10. The delivery system of claim 7 further comprising a member in rotational communication with the pinions to cause the outer sheath and the pusher to simultaneously move.

11. The delivery system of claim 10, wherein the member comprises a dial.

12. The delivery system of claim 11, wherein the dial is rotationally interlocked to the pinions and has a diameter greater than the first diameter.

13. The delivery system of claim 1, wherein the endoluminal device comprises a stent, graft, or combination thereof.

14. The stent delivery system of claim 1, wherein the endoluminal device comprises a vena cava filter.

15. The delivery system of claim 1 further comprising an inner member extending axially through the endoluminal device and the pusher and connected to a distal tip positioned distally of a distal end of the endoluminal device.

16. The delivery system of claim 1 further comprising means for actuating the linkage to cause the outer sheath to retract and the pusher to advance.

17. The delivery system of claim 16, wherein the actuating means comprises a handle in linear communication with the outer sheath.

18. The delivery system of claim 16, wherein the means comprises a slide in linear communication with the pusher.

19. The delivery system of claim 1, wherein the linkage provides transmission means for enabling a user to manipulate the linkage using less force than is required to simultaneously move the outer sheath in the first direction and the pusher in the second direction.

20. The delivery system of claim 1 further comprising indicia for indicating to a user of the delivery system when to engage or disengage the clutch mechanism.

21. A manipulator for a delivery system for an endoluminal device, the delivery system comprising an outer sheath that radially surrounds the endoluminal device in a compressed configuration and a pusher positioned at one end of the endoluminal device, the manipulator comprising a first interface for connecting the manipulator in communication with the outer sheath, a second interface for connecting the manipulator in communication with the pusher, a linkage, comprising a first pinion and a second pinion coaxially coupled to the first pinion, coupled to the first and second interface for coordinating movement of the outer sheath in a first direction with simultaneous movement of the pusher in a second direction opposite the first direction, and comprising an actuatable clutch mechanism for preventing simultaneous movement of the outer sheath and the pusher when engaged.

22. The manipulator of claim 21, wherein the manipulator is detachable from the delivery system.

23. The manipulator of claim 22, wherein the manipulator is reusable.

24. The manipulator of claim 23, wherein the manipulator comprises a material of construction adapted to withstand exposure to a predetermined temperature for a predetermined amount of time effective to sterilize the manipulator without the manipulator being damaged.

25. The manipulator of claim 24, wherein the manipulator comprises stainless steel.

26. The manipulator of claim 21 further comprising indicia for indicating to a user of the delivery system when to engage or disengage the clutch mechanism.

27. A delivery system adapted to deliver an endoluminal device from a proximal location outside a lumen to a distal location inside the lumen, the delivery system comprising:
the endoluminal device in a compressed configuration, the endoluminal device having a compressed length ($L_C$), an expanded length ($L_E$), and a foreshortening ratio $$\left(\frac{L_C - L_E}{L_E}\right)$$

greater than 0;
a proximally retractable outer sheath that radially surrounds the endoluminal device;
a distally advanceable pusher positioned at a proximal end of the endoluminal device;
a rack and pinion system in communication with both the pusher and the outer sheath that coordinates retraction of the outer sheath a first distance of retraction ($d_1$) with simultaneous advancement of the pusher a second distance of advancement ($d_2$) of the pusher, the rack and pinion system comprising a first rack attached to the outer sheath, a second rack attached to the pusher, and a pair of coaxial, rotationally-interlocked pinions supported between the first rack and the second rack, the pair of coaxial, rotationally-interlocked pinions comprising a first pinion having a first diameter ($D_1$) adapted to interface with the first rack and a second pinion ($D_2$) having a second, relatively smaller diameter adapted to interface with the second rack, wherein the gear ratio $$\left(\frac{D_2}{D_1}\right)$$

is approximately equal to the foreshortening ratio; and
an actuatable clutch mechanism for preventing simultaneous movement of the outer sheath and the pusher when engaged.

28. The delivery system of claim 27, wherein the endoluminal device comprises a vena cava filter.

29. The delivery system of claim 27, wherein the endoluminal device comprises a stent, graft, or combination thereof.

30. The delivery system of claim 29, wherein the endoluminal device comprises a stent comprising at least one portion having braided architecture and at least one portion having non-braided architecture.

31. The delivery system of claim 29, further comprising an inner member coaxial with the pusher, the outer sheath, and the stent, the inner member further comprising one or more protrusions for engaging the compressed stent.

32. The delivery system of claim 31, wherein the inner member is connected to a proximal handle and a distal tip.

33. The delivery system of claim 27 further comprising a casing surrounding the racks and pinions, wherein the clutch mechanism comprises a first member interposed between the casing and at least one of the pinions for biasing the pinions in engagement with the racks, and a second member moveable to engage one or more of the pinions, overcome the bias of the first member, and disengage the pinions from the racks.

34. The delivery system of claim 33, wherein the first member is a first spring and the second member comprises a button having a first end that protrudes from the casing and a second end that is positioned within the casing for engaging the one or more pinions, the system further comprising a second spring biasing the button in a position not in engagement with the one or more pinions.

35. The delivery system of claim 27 further comprising indicia for indicating to a user of the delivery system when to engage or disengage the clutch mechanism.

36. The delivery system of claim 35, wherein the indicia comprises a coded portion of the first rack.

37. The delivery system of claim 35, wherein the system comprises a dial rotationally interlocked with the pinions, the indicia comprises a coded portion of the dial.

38. A delivery system for an endoluminal device, the delivery system comprising:
an endoluminal device having a compressed configuration;
an outer sheath that radially surrounds the endoluminal device in the compressed configuration;
a pusher positioned at one end of the endoluminal device;

a linkage in communication with both the pusher and the outer sheath that coordinates movement of the outer sheath in a first direction with simultaneous movement of the pusher in a second direction opposite the first direction; and an actuatable clutch mechanism coupled to the linkage that reversibly disengages the linkage from the pusher or the outer sheath, or both.

* * * * *